United States Patent
Althoff et al.

(10) Patent No.: US 11,052,229 B2
(45) Date of Patent: Jul. 6, 2021

(54) DEVICES AND METHODS FOR GUIDEWIRE EXTENSION IN SPINAL SURGERY

(71) Applicant: CoreLink, LLC, St. Louis, MO (US)

(72) Inventors: Jason Althoff, St. Louis, MO (US); Nick Scodary, St. Louis, MO (US)

(73) Assignee: CoreLink, LLC, St. Louis, MO (US)

( * ) Notice: Subject to any disclaimer, the term of this patent is extended or adjusted under 35 U.S.C. 154(b) by 115 days.

(21) Appl. No.: 15/998,473

(22) Filed: Aug. 15, 2018

(65) Prior Publication Data

US 2019/0381285 A1 Dec. 19, 2019

Related U.S. Application Data

(60) Provisional application No. 62/545,574, filed on Aug. 15, 2017.

(51) Int. Cl.
*A61M 25/09* (2006.01)
*A61F 2/46* (2006.01)
*A61B 17/70* (2006.01)

(52) U.S. Cl.
CPC ..... *A61M 25/09041* (2013.01); *A61F 2/4611* (2013.01); *A61M 25/0905* (2013.01); *A61B 17/70* (2013.01)

(58) Field of Classification Search
CPC ......... A61M 25/09041; A61M 25/0905; A61F 2/4611; A61B 17/70
USPC ....................................................... 606/103
See application file for complete search history.

(56) References Cited

U.S. PATENT DOCUMENTS

| | | | | |
|---|---|---|---|---|
| 4,966,163 A * | 10/1990 | Kraus | ............... | A61M 25/0905 403/77 |
| 5,139,500 A * | 8/1992 | Schwartz | ........... | A61B 17/1697 606/103 |
| 5,295,492 A * | 3/1994 | Sellers | .............. | A61M 25/0905 600/585 |
| 6,193,706 B1 * | 2/2001 | Thorud | ............. | A61M 25/0905 604/103.04 |
| 6,491,646 B1 * | 12/2002 | Blackledge | ....... | A61M 25/0905 600/585 |
| 6,575,979 B1 * | 6/2003 | Cragg | .............. | A61B 17/32002 606/86 R |
| 2003/0028127 A1 * | 2/2003 | Balzum | ............. | A61M 25/0905 600/585 |
| 2003/0114775 A1 * | 6/2003 | Ehr | ................... | A61M 25/0905 600/585 |

(Continued)

*Primary Examiner* — Eduardo C Robert
*Assistant Examiner* — David C Comstock
(74) *Attorney, Agent, or Firm* — Stinson LLP

(57) ABSTRACT

A guidewire system for spine surgeries includes a first guidewire portion having an elongate first guidewire body with a distal end and a proximal end. A threaded male fastener at the distal end of the first guidewire body is configured to fasten to a vertebra of a spine of a subject and a threaded female coupler at the proximal end of the first guidewire body defines a threaded opening. The guidewire system includes a second guidewire portion having an elongate second guidewire body with a distal end and a proximal end. A threaded male coupler at the distal end of the second guidewire body is configured to thread into the threaded female coupler of the first guidewire portion to fasten the second guidewire portion to the first guidewire portion to form an elongate guidewire.

14 Claims, 6 Drawing Sheets

(56) References Cited

U.S. PATENT DOCUMENTS

| | | | |
|---|---|---|---|
| 2005/0137601 A1* | 6/2005 | Assell | A61B 17/1671 |
| | | | 606/79 |
| 2008/0140082 A1* | 6/2008 | Erdem | A61B 17/8805 |
| | | | 606/92 |
| 2009/0012528 A1* | 1/2009 | Aschmann | A61B 17/7065 |
| | | | 606/99 |
| 2012/0226326 A1* | 9/2012 | Overes | A61B 17/164 |
| | | | 606/329 |
| 2015/0257800 A1* | 9/2015 | Harshman | A61B 17/7208 |
| | | | 606/62 |
| 2017/0007306 A1* | 1/2017 | Werner | A61B 17/7055 |
| 2018/0303520 A1* | 10/2018 | Rajpal | A61B 17/7055 |

* cited by examiner

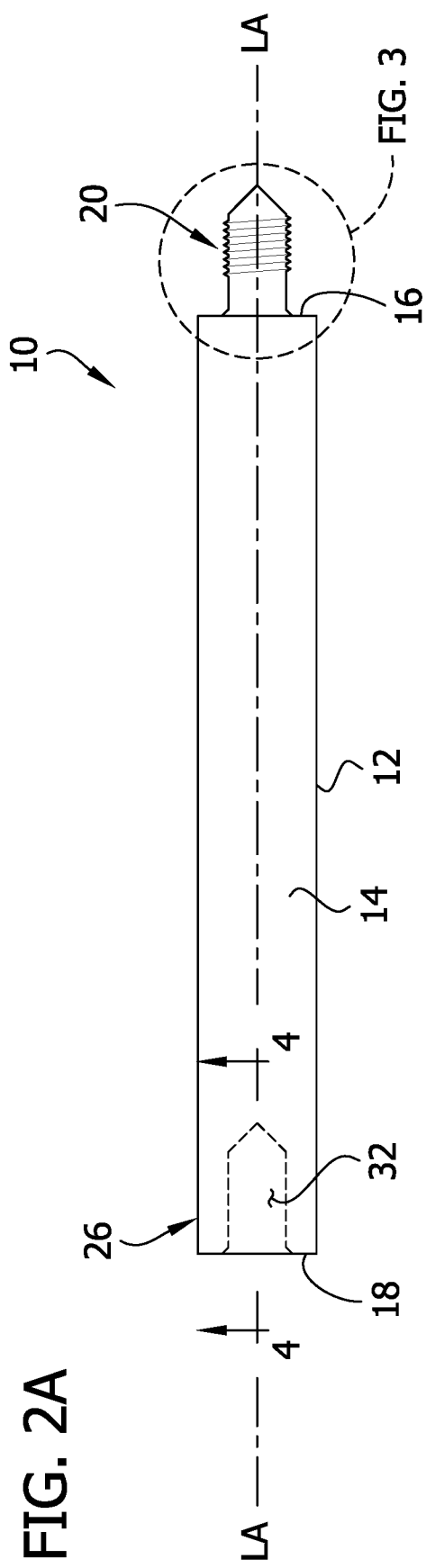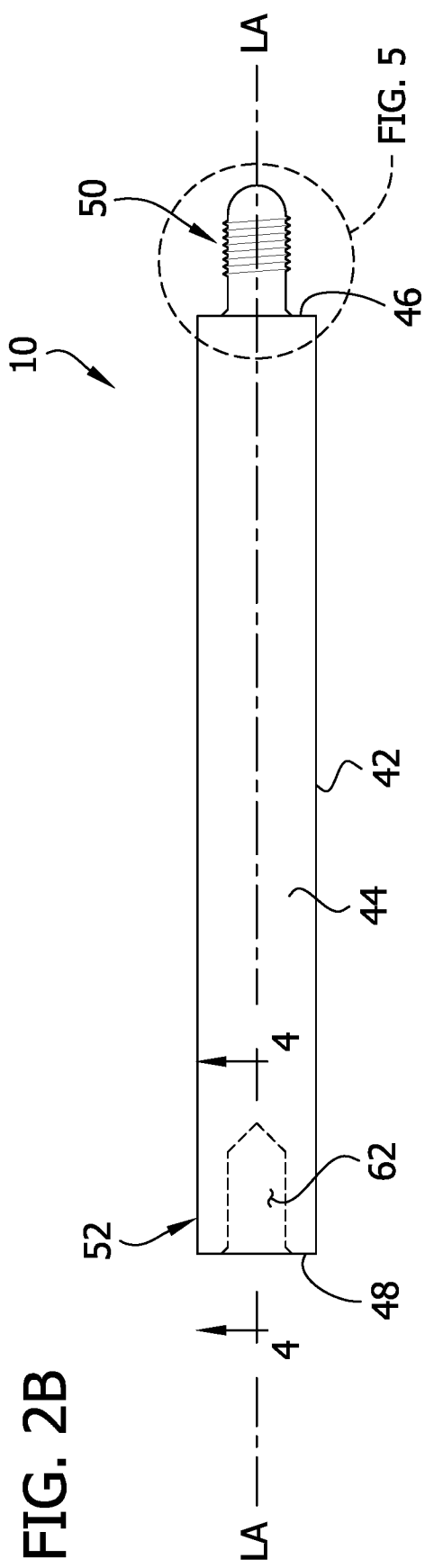

DEVICES AND METHODS FOR GUIDEWIRE EXTENSION IN SPINAL SURGERY

CROSS-REFERENCE TO RELATED APPLICATION

The present application claims the benefit of U.S. Provisional Application No. 62/545,574, filed on Aug. 15, 2017, the entirety of which is hereby incorporated by reference.

FIELD OF THE DISCLOSURE

The present disclosure generally relates to spinal surgery guidewires and methods.

BACKGROUND

Spinal surgeries, including sacroiliac joint fusion, often utilize guidewires that anchor into the spine to guide surgical instruments, etc. to the correct position. Generally, prior art guidewires are only one piece with a non-adjustable length.

SUMMARY

In one aspect, a guidewire system for spine surgeries generally comprises a first guidewire portion including an elongate first guidewire body having a distal end, a proximal end, and a longitudinal axis extending between the distal and proximal ends. A threaded male fastener at the distal end of the first guidewire body extends distally therefrom. The threaded male fastener is configured to fasten to a vertebra of a spine of a subject. A threaded female coupler extends distally from the proximal end of the first guidewire body and defines a threaded opening. A second guidewire portion includes an elongate second guidewire body having a distal end, a proximal end, and a longitudinal axis extending between the distal and proximal ends. A threaded male coupler at the distal end of the second guidewire body extends distally therefrom. The threaded male coupler is adapted to thread into the threaded female coupler of the first guidewire portion to fasten the second guidewire portion to the first guidewire portion to form an elongate guidewire.

In another aspect, a guidewire for spinal surgeries generally comprises an elongate guidewire body including a distal end, a proximal end, and a longitudinal axis extending between the distal and proximal ends. A threaded male fastener at the distal end of the guidewire body extends distally therefrom. The threaded male fastener is adapted to thread into a vertebra of a spine of a subject. A threaded female coupler extends distally from the proximal end of the guidewire body.

In yet another aspect, a surgical method generally comprises threading a threaded male fastener of a first guidewire portion into a vertebra of a spine of a subject to anchor the first guidewire portion to the spine. The threaded male fastener is at a distal end of an elongate first guidewire body of the first guidewire portion. A threaded male coupler of a second guidewire portion is threaded into a threaded female coupler at a proximal end of the first guidewire portion to attach the second guidewire portion to the first guidewire portion, thereby creating an elongate guidewire.

Other aspects and features will be in part apparent and in part pointed out hereinafter.

BRIEF DESCRIPTION OF THE DRAWINGS

FIG. 2A is an elevation of a first guidewire portion of a guidewire system;

FIG. 2B is an elevation of a second guidewire portion of the guidewire system;

Corresponding reference characters indicate corresponding parts throughout the drawings.

DETAILED DESCRIPTION

Figure 1:
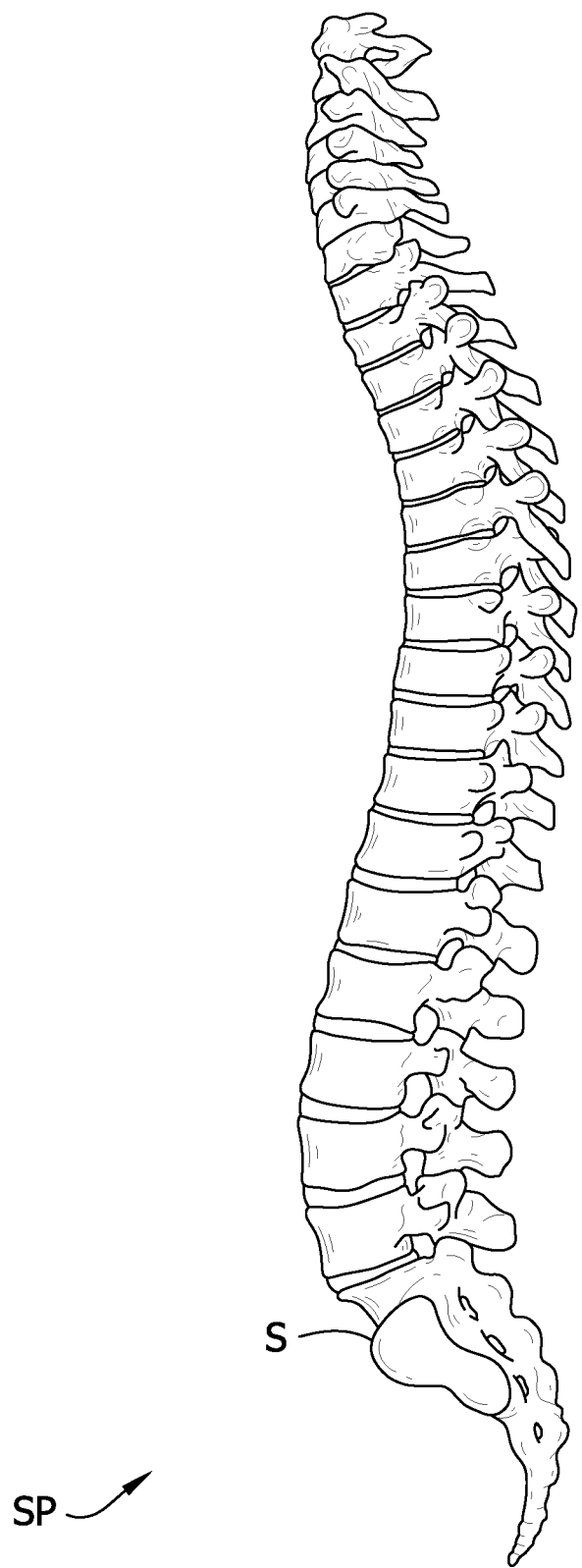
FIG. 1 is a side elevation of a human spine.

Referring to FIG. 1, a spine is generally indicated at SP. Near the bottom of the spine, the sacrum is indicated at S. The present application discloses methods and associated devices applicable to multiple spinal surgeries and includes sacroiliac joint SIJ fusion as a non-limiting example. The devices and methods disclosed are well-suited to SU fusion, but it will be apparent to one of skill in the art that other applications are possible without departing from the scope of the present disclosure.

Referring to FIGS. 2A and 2B, a guidewire system for a spinal surgery is generally indicated at 10. A first guidewire portion 12, which can also be considered a guidewire, is configured to be anchored to a vertebra of the spine, and a second guidewire portion 42, which can also be considered a guidewire extender, is configured to thread into the first guidewire portion 12 to provide a guidewire of a length appropriate for the surgery. More specifically, the first guidewire portion 12 comprises a threaded female coupler, generally indicated at 26, and the second guidewire portion 42 comprises a threaded male coupler, generally indicated at 50, which threads into (e.g., connects to) the threaded female coupler 26. This arrangement allows a surgeon to use the first guidewire portion 12 without regard to whether it is long enough. If the first guidewire portion 12 is not long enough, then the second guidewire portion 42 is used to extend the length of the guidewire system 10. The second guidewire portion 42 does not need to be used if the length of the first guidewire portion 12 is suitable. Examples of factors that affect how much guidewire length is necessary include the size of a subject undergoing surgery and the type of surgery. In addition, it may be beneficial to initially use the first guidewire portion 12 for installing in the spine SP since the first guidewire portion will be shorter, less likely to bend, and easier to control than a guidewire having an increased length, such as the combination of the first and second guidewire portions 10. However, the shorter guidewire (e.g., the first guide portion 12) may only have a short exposed length extending outside the patient's body, making it difficult to pass instrumentation over it. Often times when switching from a drill to a screw driver, for example, the guidewire can unintendedly travel, particularly when not exposed behind a working instrument. Because the sacral foramina have exiting nerves, it is dangerous to have traveling guidewires in SIJ fusion (as well as percutaneous pedicle screws in the lumbar spine for anterior vascular risks). The guidewire extender (e.g., second guidewire portion) 42 allows for a shorter initial guidewire portion 12 to be secured into desired anatomic location and then the guidewire system 10 can be extended when needed. This provides a control point when removing and inserting other instrumentation and helps prevent unintended guide wire travel to neural of vascular structures.

The first guidewire portion 12 comprises an elongate first guidewire body 14 having a distal end 16, a proximal end 18, and a longitudinal axis LA, extending between the distal and proximal ends. The first guidewire portion 12 further comprises a threaded male fastener, generally indicated at 20, which extends distally from the distal end 16 of the first guidewire body 14 along the longitudinal axis LA. The threaded female coupler 26 extends distally along the longitudinal axis LA from the proximal end 18 of the first guidewire body 14. In an embodiment, the first guidewire portion 12 has a length extending between the proximal and distal ends 18, 16 of, for example, about 300 mm, or from about 200 mm and about 400 mm, although other lengths are within the scope of the present disclosure.

Figure 3:
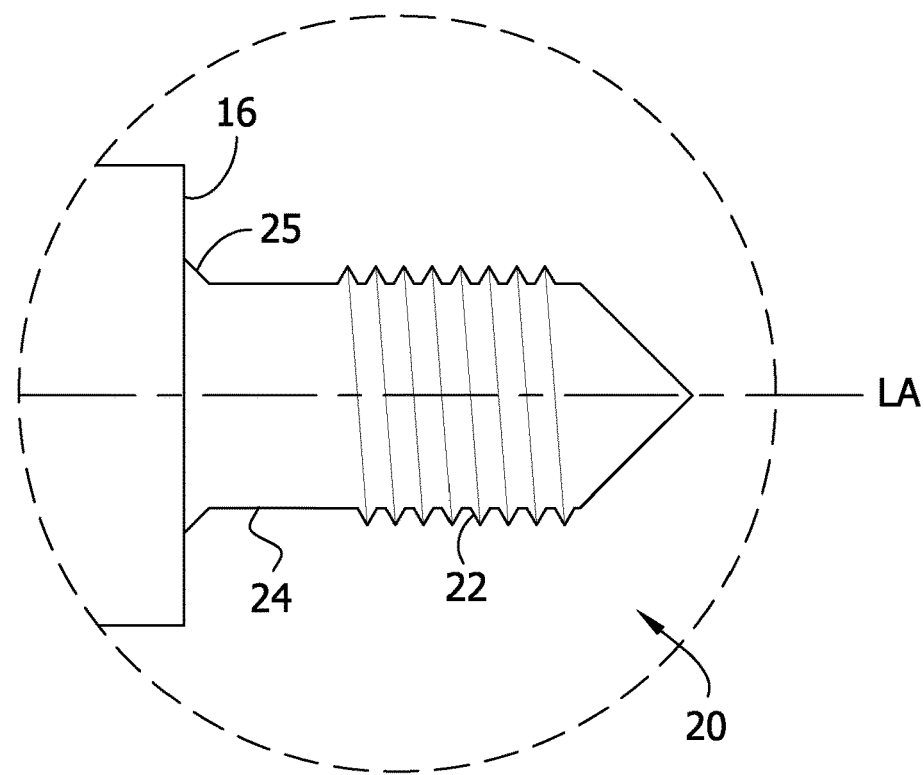
FIG. 3 is an enlarged view of a section of the first guidewire portion as indicated in FIG. 2A.

Referring to FIG. 3, the threaded male fastener 20 comprises a non-threaded section 24 and a threaded section 22. While the threaded male fastener 20 can be any of various types of fasteners in other embodiments, in the illustrated embodiment it is a self-tapping screw. The non-threaded section 24 extends distally along the longitudinal axis LA from a location at or near the distal end 16 of the first guidewire body 14 toward the threaded section 22. A bevel 25 located at the distal end 16 of the first guidewire body 14 can be included adjacent to or as part of the threaded male fastener 20. The threaded section 22 of the threaded male fastener 20 extends distally along the longitudinal axis LA to a free end that defines a point. In other embodiments the free end may define a shape other than a point or the threaded section 22 may not extend to the free end of the first guidewire portion 12. Preferably, the threaded male fastener 20 is configured to thread directly into (e.g., attach to) the vertebra, but as explained below, the threaded male fastener can also be configured to attach to a separate spinal anchor. Other embodiments are possible; for example, certain embodiments have male fasteners 20 without a non-threaded section 24. Some embodiments, including some embodiments configured for use with a spinal anchor, include male fasteners 20 that form a bolt, non-self-tapping screw, or other type of fastener. In yet other embodiments, the male fastener 20 may not be threaded and may be configured to be secure to the sacrum S or other vertebra in other ways.

Figure 4:
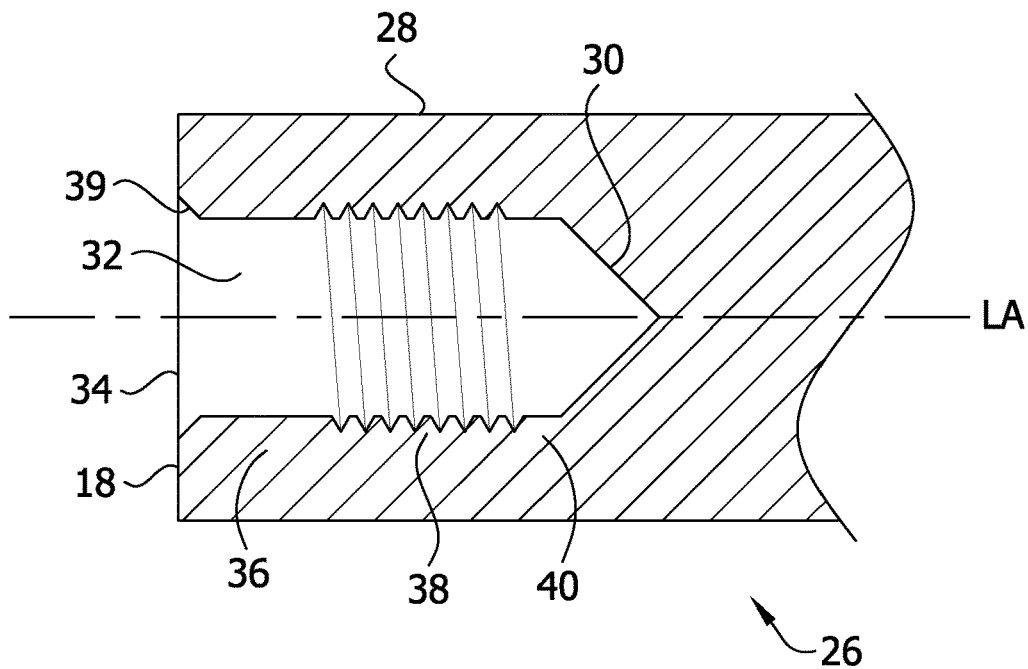
FIG. 4 is an enlarged fragmentary section taken through line 4-4 in FIG. 2A.

Referring to FIG. 4, the threaded female coupler 26 comprises an annular wall 28 and a distal wall 30. In the illustrated embodiment, the distal wall 30 has a generally conical shape, but in other embodiments it can be other shapes such as a flat and circular. The annular wall 28 defines a threaded opening (e.g., male fastener receiving space) 32 and an entrance 34 at the proximal end 18 into the threaded opening 32. While the illustrated embodiment has cylindrical guidewire portions 12, 42 with a threaded opening 32 (e.g., tapped hole) along the longitudinal axes LA of the guidewire portions, other shapes for the threaded female coupler 26 are also contemplated within the scope of the disclosure.

The annular wall 28 comprises a shank section 36, a threaded section 38, and a clearance section 40. The shank section 36 is generally smooth and extends from a location at or near the proximal end 18 of the first guidewire body 14 distally along the longitudinal axis LA towards the threaded section 38. The shank section 36 may include or be adjacent to a bevel 39 at the proximal end 18 of the first guidewire body 14. The threaded section 38 extends distally from the shank section 36 towards the clearance section 40, and is configured to engage the threaded male coupler 50 of the second guidewire portion 42. The clearance section 40 is generally smooth and extends distally from the threaded section 38 towards the distal wall 30. In other embodiments, by way of example, the threaded section 38 could extend further along the longitudinal axis in either the proximal or distal direction or both directions, eliminating the clearance section 40, the shank section 36, or both. A taper could also be used in place of the bevel 39, or the bevel 39 could simply be omitted, among other changes that could be made without departing from the scope of the present disclosure.

The distal wall 30 defines the distal boundary of the threaded opening 32. In a preferred embodiment, the free end of the threaded male coupler 50 is spaced a distance along the longitudinal axis LA from the distal wall 30 even when the threaded male coupler 50 is fully threaded with the female threaded coupler 26. In this way, guidewire systems 10 with airtight threads provide room for any air trapped by the threads. Other embodiments are also possible within the scope of the disclosure.

Referring again to FIG. 2B, the second guidewire portion 42 comprises an elongate second guidewire body 44 having distal and proximal ends 46, 48 and a longitudinal axis LA extending between the distal and proximal ends. The second guidewire portion 42 further comprises a threaded male coupler, generally indicated at 50, extending distally from the distal end 46 of the second guidewire body 44 along the longitudinal axis LA. A second threaded female coupler 52 extends distally along the longitudinal axis LA from the proximal end 48 of the second guidewire body 44, and defines a second threaded opening 62. The second threaded female coupler 52 and second threaded opening 62 are the same as threaded female coupler 26 and opening 32, respectively. Other embodiments may vary significantly from this exemplary illustration. For example, the second threaded female coupler 52 may be entirely absent in some embodiments. In an embodiment the second guidewire portion 42 has a length extending between the proximal and distal ends 48, 46 of, for example, about 300 mm, or from about 200 mm to about 400 mm, although other lengths are within the scope of the present disclosure.

Figure 5:
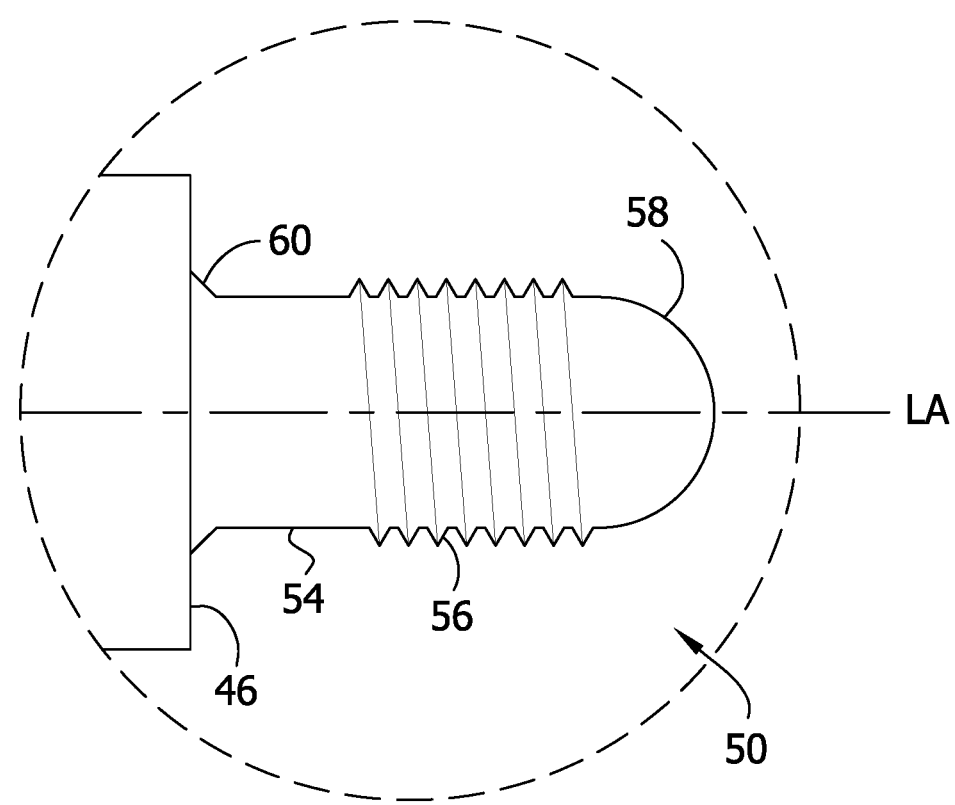
FIG. 5 is an enlarged view of a section of the second guidewire portion as indicated in FIG. 2B.

Referring to FIG. 5, the threaded male coupler 50 of the second guidewire portion 42 is configured to thread into the threaded female coupler 26 of the first guidewire portion 12. The threaded male coupler 50 comprises a shank section 54, a threaded section 56, and a rounded end (e.g., free end) 58. The lengths of the threaded section 56 and the shank section 54 of the threaded male coupler 50 generally correspond to the lengths of the threaded section 38 and the shank section 36 of the threaded female coupler 26, respectively. The shank section 54 is generally smooth and extends distally along the longitudinal axis LA from a location at or near the distal end 46 of the second guidewire body 44 towards the threaded section 56. The shank section 54 may include or be adjacent to a bevel 60 at the distal end 46 of the second guidewire body 44. The threaded section 56 extends distally, and is configured to engage the threaded female coupler 26 of the first guidewire body 14, specifically the threaded section 38. The rounded end 58 extends distally from a location near the end of the threaded section 56 and is generally smooth. Preferably, the rounded end 58 has a length along the longitudinal axis LA of less than the length along the longitudinal axis LA of the clearance section 40 of the threaded female fastener 26. In other words, in the preferred embodiment, the length of the threaded opening 32 of the threaded female fastener 26 between the proximal end 18 and the distal wall 30 is greater than the length of the threaded male coupler 50 between the distal end 46 and the rounded end (e.g., free end) 58 so that the male coupler can be completely inserted into the female coupler with room to spare. In one embodiment, the rounded end 58 has a sufficient length, such as a length equal to or greater than the length of the threaded section 56, so that the rounded end 46 helps facilitate the connection (e.g., insertion) of the male coupler 50 into the female coupler 26 (e.g., the rounded end helps guide the male coupler 50 into the female coupler). In other embodiments, by way of example, the threaded section 56 could extend further along the longitudinal axis LA in either the proximal or distal direction or both directions, eliminating the rounded end 58, the shank section 54, or both. The rounded end 58 could be shaped differently, for example, flat, among other changes that could be made without departing from the scope of the present disclosure. In one embodiment, the distal wall 30 of the female coupler 26 is shaped to correspond to the shape of the end 58 of the male coupler 50.

The configuration presented of the threaded female coupler 26 and the threaded male coupler 50 allows the first guidewire portion 12 and the second guidewire portion 42 to thread (e.g., connect) together. In a preferred embodiment, the connection also allows the distal end 46 of the second guidewire body 44 to mate (e.g., engage) with the proximal end 18 of the first guidewire body 14 when the threads are fully engaged. Preferably, the threads are designed so the guidewire system can be threaded until the guidewire portions mate and so that when the guidewire portions mate, the threads are tight. Preferably, the first guidewire portion 12 and the second guidewire portion 42 are also of equal outer diameters, for example about 0.125 inches across or between 0.075 and 0.25 inches, so that the guidewire system 10 forms an almost smooth outer surface of the guidewire even at the point where the guidewire portions meet.

The first guidewire portion 12 and the second guidewire portion 42 are identical in some embodiments. In such an embodiment, the threaded male coupler 50 and threaded male fastener 20 are preferably designed in accordance with the description of the threaded male fastener 20. The threaded female couplers 26, 52 on both guidewire portions 12, 42 are configured to threadably receive the interchangeable threaded male fastener 20 or threaded male coupler 50. Such an embodiment is generally easier and cheaper to manufacture because only one unique part or no unique part is manufactured. Moreover, the threads in the threaded sections 22, 38, 46 of the first and second guidewire portions 12, 42 can be right-handed threads (e.g., standard threads) or left-handed threads (e.g., reversed-threads).

In another aspect, a surgical method comprises anchoring a first guidewire portion to a vertebra or sacrum of the spine and threading a second guidewire portion into the first guidewire portion. In some embodiments, the first guidewire portion is configured to be usable without the second guidewire portion, and the second guidewire portion is only used when needed or convenient, for example when operating on a larger patient.

Figure 6:
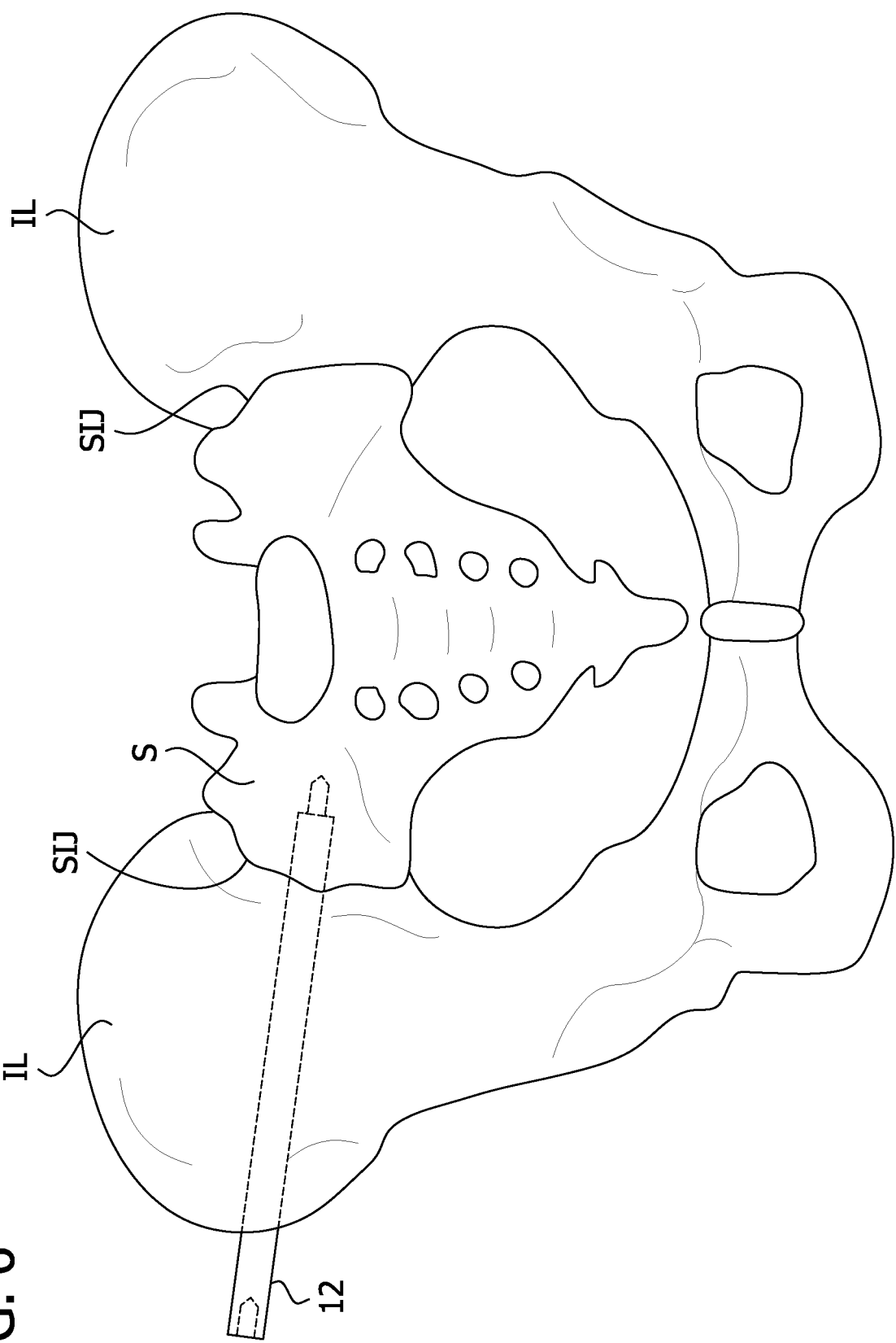
FIG. 6 is a front elevation of a first guidewire portion threading into the sacrum.
Figure 7:
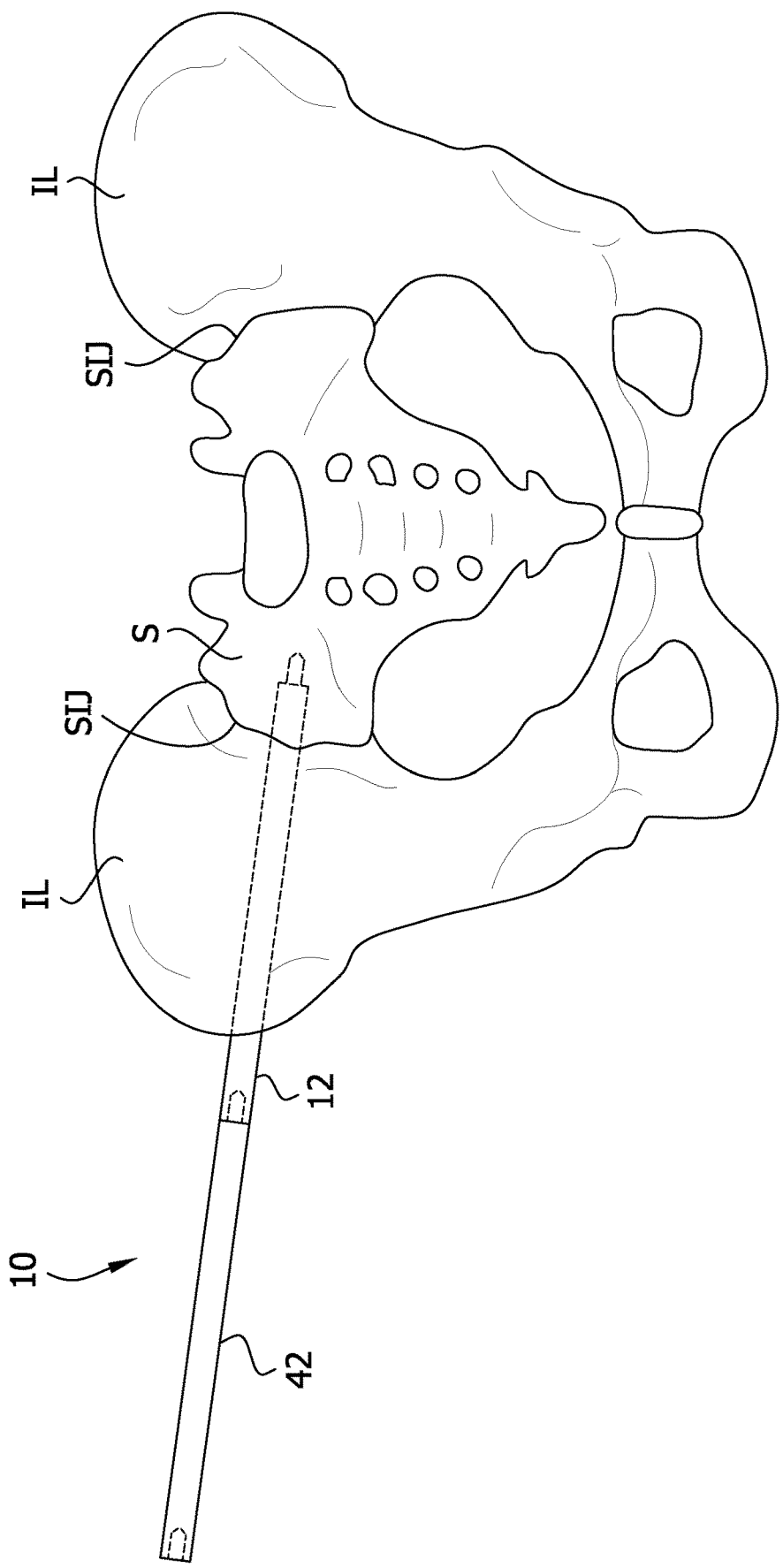
FIG. 7 is a front elevation of a second guidewire portion threading into a first guidewire portion that is threaded into the sacrum.

FIGS. 6 and 7 illustrate a surgical method as applied to sacroiliac joint fusion (SU fusion) using a first guidewire portion 12 and a second guidewire portion 42. A sacroiliac joint SU and surrounding bones are shown in FIGS. 6 and 7. In SU fusion, an ilium IL of a subject is mechanically fastened to a sacrum S of the subject to force them to grow together. The sacroiliac joint SIJ is a large joint that forms where the sacrum S and the ilium IL meet. In cases where SIJ fusion is found appropriate, preferably a subject lays down on an operating table, is sedated, and an operating corridor is made, all according to methods known in the art. In the embodiment illustrated, the guidewire system 10 disclosed in FIGS. 2-5 and the accompanying description is used.

Referring to FIG. 6, a first guidewire portion 12 of the guidewire system 10 is then, after the operating corridor is made, anchored to the sacrum S of the spine of the subject. The guidewire portion 12 is generally positioned near the middle of the operative corridor. Preferably the first guidewire portion 12 threads directly into the sacrum S. Alternatively, a separate spinal anchor (not shown) may be used, in which case the spinal anchor attaches at or near the sacrum S and the first guidewire portion 12 attaches to the spinal anchor.

Referring to FIG. 7, the second guidewire portion 42 is then threaded into the first guidewire portion 12 to form an elongate guidewire system 10 of an appropriate length. In some methods, the surgeon will first evaluate whether an extra length is needed. When the guidewire system 10 is installed, any necessary surgical instruments and tools can be guided precisely to the right point. As will be apparent to one skilled in the art, the same method and similar methods can be practiced in a variety of spinal surgeries without departing from the scope of the disclosure. Among other differences, applying such a method to other surgeries varies from the previous description in that a different vertebra may be used. For example, the second guidewire portion 42 may be used for percutaneous pedicle screw placement and/or imaged guided placement of pedicle screws.

In all embodiments, the guidewire portions 12, 42 are preferably made from a surgical-grade material that is easy to sterilize. By way of non-limiting example, stainless steel or titanium can be used. In other embodiments, the guidewire portions 12, 42 are sealed in sterile containers and intended for single use only.

In other embodiments, more than two guidewire portions 12, 42 form the extended guidewire system 10. For example, additional (e.g., third, fourth, fifth, etc.) guidewire extenders (e.g., second guidewire portions) 42 may successively added in series to the first guidewire extender connected to the first guidewire portion 12 to create an elongate guidewire system 10 of any desired length.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:
1. A guidewire system for spine surgeries comprising:
  a first guidewire portion including
    an elongate first guidewire body having a distal end, a proximal end, and a longitudinal axis extending between the distal and proximal ends,
    a threaded male fastener at the distal end of the first guidewire body and extending distally therefrom, the threaded male fastener being configured to fasten to a vertebra of a spine of a subject, and a threaded female coupler extending distally from the proximal end of the first guidewire body and defining a threaded opening; and a second guidewire portion including an elongate second guidewire body having a distal end, a proximal end, and a longitudinal axis extending between the distal and proximal ends, and a threaded male coupler at the distal end of the second guidewire body and extending distally therefrom, the threaded male coupler being adapted to thread into the threaded female coupler of the first guidewire portion to fasten the second guidewire portion to the first guidewire portion to form an elongate guidewire, wherein the first guidewire portion is identical to the second guidewire portion.

2. The guidewire system of claim 1 wherein the male fastener is adapted to fasten to the vertebra indirectly through use of a spinal anchor.

3. The guidewire system of claim 1 wherein a threaded section of the threaded female coupler is spaced at a distance along the longitudinal axis from the proximal end of the first guidewire body, and the threaded male coupler is insertable along said distance without threading.

4. The guidewire system of claim 1 wherein the proximal end of the first guidewire portion is configured to mate with the distal end of the second guidewire portion when the threaded male coupler is threaded into the threaded female coupler.

5. The guidewire system of claim 4 wherein the male coupler of the second guidewire portion has a rounded distal end.

6. The guidewire system of claim 4, the threaded female coupler of the first guidewire portion further comprising:
a wall defining a threaded hole;
a threaded section wherein the wall is threaded; and
a shank section wherein the wall is not threaded, the shank section located between the threaded section and the proximal end of the first guidewire body.

7. The guidewire system of claim 1 wherein the threaded male fastener is configured to thread into a vertebra of a spine of a subject.

8. The guidewire system of claim 7, the threaded female coupler of the first guidewire further comprising a wall defining the threaded opening, the wall having:
a threaded section; and
a shank section between the proximal end of the first guidewire portion and the threaded section; and
the threaded male coupler of the second guidewire portion further comprising:
a threaded section; and
a non-threaded shank section between the threaded section and the distal end of the second guidewire portion, the shank section adapted to fit in the shank section of the female threaded coupler when the threaded male coupler is threaded into the threaded female.

9. The guidewire system of claim 7, further comprising a third guidewire portion, the third guidewire portion comprising
an elongate third guidewire body having a distal end, a proximal end, and a longitudinal axis extending between the distal and proximal ends, and
a threaded male coupler at the distal end of the third guidewire body and extending distally therefrom, the threaded male coupler of the third guidewire portion being adapted to thread into the threaded female coupler of the first guidewire portion to fasten the third guidewire portion to the first guidewire portion to form an elongate guidewire;

and wherein the second guidewire portion has a length and the third guidewire portion has a length different from the length of the second guidewire portion.

10. A guidewire system for spinal surgeries comprising:
a guidewire including
an elongate guidewire body including a distal end, a proximal end, and a longitudinal axis extending between the distal and proximal ends;
a threaded male fastener at the distal end of the guidewire body and extending distally therefrom, the threaded male fastener being adapted to thread into a vertebra of a spine of a subject, and
a threaded female coupler extending distally from the proximal end of the guidewire body;
a first guidewire extender including
a first elongate extender body including a distal end, a proximal end, and a longitudinal axis extending between the distal and proximal ends; and
a first threaded male coupler extending along the longitudinal axis from the distal end, the first threaded male coupler configured to thread into the threaded female coupler of the guidewire; and
a second guidewire extender including
a second elongate extender body including a distal end, a proximal end, and a longitudinal axis extending between the distal and proximal ends; and
a second threaded male coupler extending along the longitudinal axis from the distal end, the second threaded male coupler configured to thread into the threaded female coupler of the guidewire;
wherein the first guidewire extender has a length and the second guidewire extender has a length different from the length of the first guidewire extender.

11. The guidewire system of claim 10, wherein the proximal end of the guidewire and the distal end of a guidewire extender mate when the guidewire extender is fully threaded into the guidewire.

12. A surgical method comprising:
threading a threaded male fastener of a first guidewire portion into a vertebra of a spine of a subject to anchor the first guidewire portion to the spine, wherein the threaded male fastener is at a distal end of an elongate first guidewire body of the first guidewire portion;
threading a threaded male coupler of a second guidewire portion into a threaded female coupler at a proximal end of the first guidewire portion to attach the second guidewire portion to the first guidewire portion, thereby creating an elongate guidewire,
wherein the step of threading the threaded male faster of the first guidewire portion into the vertebra comprises threading the threaded male fastener into a separate anchor piece and anchoring the anchor piece to the vertebra.

13. The surgical method of claim 12 wherein the step of threading the male coupler into the threaded female coupler comprises threading the male coupler into the threaded female coupler until the proximal end of the first guidewire portion mates with a distal end of the second guidewire portion.

14. The surgical method of claim 12 wherein the vertebra is the sacrum.

* * * * *